United States Patent

Li et al.

(10) Patent No.: US 10,094,751 B2
(45) Date of Patent: Oct. 9, 2018

(54) SYSTEM AND METHOD FOR DETERMINING DIRECT DAMAGE TOLERANCE ALLOWABLES

(71) Applicant: Bell Helicopter Textron Inc., Fort Worth, TX (US)

(72) Inventors: Xiaoming Li, Colleyville, TX (US); Bogdan R. Krasnowski, Bedford, TX (US)

(73) Assignee: Bell Helicopter Textron Inc., Fort Worth, TX (US)

( * ) Notice: Subject to any disclaimer, the term of this patent is extended or adjusted under 35 U.S.C. 154(b) by 145 days.

(21) Appl. No.: 15/079,946

(22) Filed: Mar. 24, 2016

(65) Prior Publication Data

US 2016/0282244 A1  Sep. 29, 2016

Related U.S. Application Data

(60) Provisional application No. 62/137,427, filed on Mar. 24, 2015.

(51) Int. Cl.
*G01N 3/08* (2006.01)
*G01N 3/32* (2006.01)

(52) U.S. Cl.
CPC ............ *G01N 3/08* (2013.01); *G01N 3/32* (2013.01); *G01N 2203/0066* (2013.01)

(58) Field of Classification Search
None
See application file for complete search history.

(56) References Cited

U.S. PATENT DOCUMENTS

| 3,774,443 A | * | 11/1973 | Green | G01B 17/04 |
| | | | | 73/577 |
| 3,957,450 A | * | 5/1976 | Salt | G01N 3/00 |
| | | | | 416/219 A |
| 3,983,745 A | * | 10/1976 | Juusola | G01N 3/32 |
| | | | | 73/789 |
| 4,090,401 A | | 5/1978 | Yamamoto et al. | |
| 4,090,489 A | * | 5/1978 | Barker | G01N 3/20 |
| | | | | 125/13.01 |
| 4,116,049 A | * | 9/1978 | Barker | G01N 3/08 |
| | | | | 73/87 |
| 4,164,874 A | * | 8/1979 | Cassatt | G01B 3/00 |
| | | | | 73/799 |

(Continued)

OTHER PUBLICATIONS

European Search Report, dated Nov. 24, 2016, by the EPO, re EP Patent Application No. 16162437.

(Continued)

*Primary Examiner* — Harshad R Patel
*Assistant Examiner* — Tran M Tran
(74) *Attorney, Agent, or Firm* — Timmer Law Group, PLLC

(57) ABSTRACT

A method of determining damage tolerance allowables in a specimen, the method includes applying a cyclic load to a specimen until a first crack emanates from a notch in the specimen, the cyclic load having a maximum load and a minimum load. The method also includes applying a subsequent cyclic load to the specimen until the first crack grows to form a second crack emanating from the first crack, the subsequent cyclic load having the same maximum load but a greater minimum load.

18 Claims, 14 Drawing Sheets

(56) References Cited

U.S. PATENT DOCUMENTS

| | | | | | |
|---|---|---|---|---|---|
| 4,299,120 | A * | 11/1981 | Barker | ............... | G01N 3/32 73/799 |
| 4,590,804 | A * | 5/1986 | Brull | ............... | G01L 1/06 73/762 |
| 4,895,027 | A * | 1/1990 | Manahan, Sr. | ............... | G01N 3/00 73/794 |
| 5,078,843 | A * | 1/1992 | Pratt | ............... | C04B 41/5144 205/118 |
| 5,079,955 | A * | 1/1992 | Eberhardt | ............... | G01N 3/30 324/693 |
| 5,654,500 | A * | 8/1997 | Herron | ............... | G01N 3/00 73/112.01 |
| 6,405,600 | B1 * | 6/2002 | Matic | ............... | G01N 3/02 73/799 |
| 6,588,283 | B2 * | 7/2003 | Wang | ............... | G01N 3/22 73/799 |
| 7,230,421 | B2 * | 6/2007 | Goldfine | ............... | G01B 7/24 324/240 |
| 7,320,242 | B2 * | 1/2008 | Hoo Fatt | ............... | G01N 3/30 73/12.14 |
| 7,480,573 | B2 * | 1/2009 | Toyosada | ............... | G01N 3/32 702/34 |
| 7,533,557 | B1 * | 5/2009 | Mott | ............... | G01N 3/303 73/12.14 |
| 7,623,973 | B1 * | 11/2009 | Wang | ............... | G01M 5/0033 702/185 |
| 7,994,781 | B2 * | 8/2011 | Goldfine | ............... | B24B 21/06 324/202 |
| 8,109,150 | B2 * | 2/2012 | Sato | ............... | G01N 3/00 702/181 |
| 8,176,795 | B2 * | 5/2012 | Wang | ............... | G01N 35/00 73/847 |
| 8,479,588 | B1 * | 7/2013 | Simkins, Jr. | ............... | G06F 17/5009 73/799 |
| 8,571,814 | B2 * | 10/2013 | Zhao | ............... | G06Q 10/04 702/34 |
| 8,610,883 | B2 * | 12/2013 | Lam | ............... | G01B 11/168 356/33 |
| 8,763,229 | B2 * | 7/2014 | Reid | ............... | E04G 23/0244 29/402.01 |
| 8,984,955 | B2 * | 3/2015 | Mouri | ............... | B23P 6/04 73/788 |
| 9,109,979 | B2 * | 8/2015 | Dietrich | ............... | G01N 3/08 |
| 9,222,865 | B2 * | 12/2015 | Khonsari | ............... | G01N 3/34 |
| 9,243,985 | B2 * | 1/2016 | Khonsari | ............... | C22C 38/00 |
| 9,280,620 | B2 * | 3/2016 | Amann | ............... | G06F 17/5018 |
| 9,383,303 | B2 * | 7/2016 | Bruchhausen | ............... | G01N 3/12 |
| 9,423,330 | B2 * | 8/2016 | Mary | ............... | G01N 29/043 |
| 9,464,975 | B2 * | 10/2016 | Esposito | ............... | G01N 3/08 |
| 9,476,815 | B2 * | 10/2016 | Khonsari | ............... | G01N 3/32 |
| 9,573,284 | B2 * | 2/2017 | Thwing | ............... | B26D 3/14 |
| 9,702,798 | B1 * | 7/2017 | Kim | ............... | G01N 3/42 |
| 9,841,364 | B2 * | 12/2017 | Chen | ............... | G01N 3/34 |
| 2009/0315540 | A1 * | 12/2009 | Goldfine | ............... | B24B 21/06 324/202 |
| 2011/0005329 | A1 * | 1/2011 | Matsuoka | ............... | G01N 3/34 73/799 |
| 2015/0114697 | A1 * | 4/2015 | Murrell | ............... | H01G 4/232 174/255 |
| 2016/0061688 | A1 * | 3/2016 | Van Wittenberghe | ............... | G01M 3/2853 73/577 |
| 2016/0349161 | A1 * | 12/2016 | Chen | ............... | G01N 3/32 |

OTHER PUBLICATIONS

Brett L. Anderson, et al; Evaluation and Verification of Advanced Methods to Assess Multiple-Site Damage of Aircraft Structure; Oct. 2004; URL: https://web.archive.org/web/20111018161217/http://airportaircraftsafetyrd.tc.faa.gov/Programs/agingaircraft/Structural/reports/04-42-Vol-I.pdf, (Nov. 18, 2016).

K.A. Zakaria, et al.; Fractography Analysis of A16061 Under Fatigue Spectrum Loadings; Engineering e-Transaction, vol. 7, No. 1, Jun. 2012, pp. 28-33.

ASTM Iinternational, Standard Test Method for Measurement of Fatigue Crack Growth Rates, Apr. 2008, 46 pages, Pennsylvania, United States.

EP Communication under Rule 71(3) EPC, dated May 18, 2018, by the EPO, re EP Patent App No. 16162437.4.

* cited by examiner

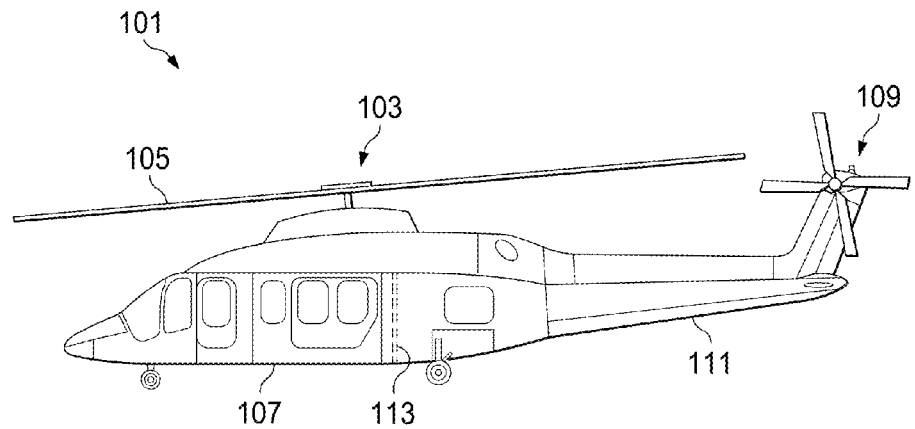
FIG. 1
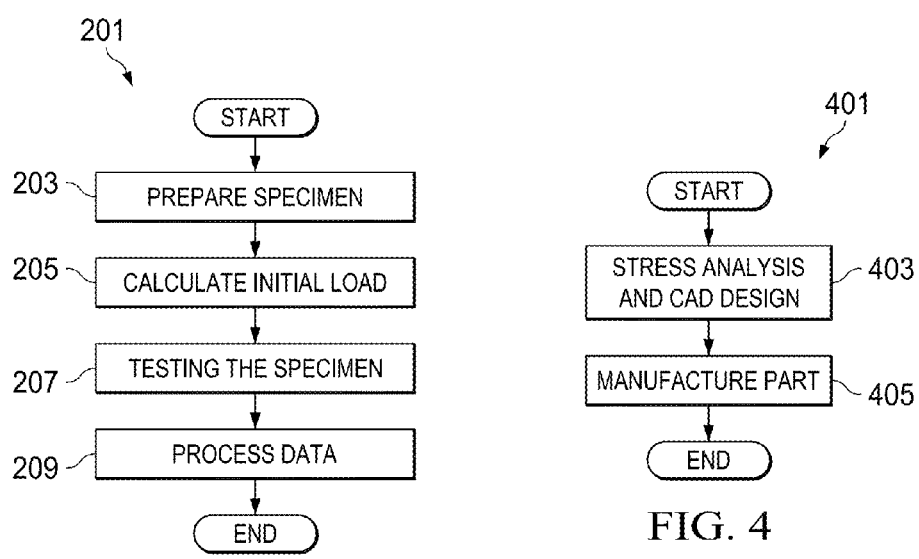
FIG. 2
FIG. 4

FIG. 3

| $c_1/c_2$ | $c_1/b_1$ | $c_2/b_2 = 0.0$ | | $c_2/b_2 = 0.1$ | | $c_2/b_2 = 0.2$ | | $c_2/b_2 = 0.5$ | | $c_2/b_2 = 0.8$ | | $c_2/b_2 = 1.0$ | |
|---|---|---|---|---|---|---|---|---|---|---|---|---|---|
| | | a-tip | c-tip | a-tip | c-tip | a-tip | c-tip | a-tip | c-tip | a-tip | c-tip | a-tip | c-tip |
| 0.0 | 0.0 | 0.996 | 1.931 | 1.000 | 2.024 | 0.996 | 1.907 | 1.003 | 1.906 | 1.000 | 1.870 | 1.004 | 1.846 |
| | 0.1 | 1.062 | 1.930 | 1.068 | 1.973 | 1.069 | 1.924 | 1.069 | 1.795 | 1.057 | 1.705 | 1.055 | 1.645 |
| | 0.2 | 1.191 | 2.009 | 1.196 | 2.021 | 1.200 | 2.005 | 1.191 | 1.914 | 1.182 | 1.854 | 1.174 | 1.814 |
| | 0.5 | 1.766 | 2.817 | 1.786 | 2.874 | 1.816 | 2.909 | 1.935 | 3.034 | 2.070 | 3.171 | 2.187 | 3.278 |
| | 0.8 | 2.524 | 4.427 | 2.606 | 5.038 | 2.715 | 5.389 | 3.291 | 6.605 | 4.126 | 7.951 | 4.832 | 8.979 |
| | 1.0 | 3.140 | 5.955 | 3.278 | 7.366 | 3.471 | 8.289 | 4.635 | 11.871 | 6.432 | 15.372 | 7.925 | 17.706 |
| 0.2 | 0.0 | 1.037 | 1.280 | 1.041 | 1.285 | 1.043 | 1.291 | 1.070 | 1.330 | 1.102 | 1.390 | 1.128 | 1.441 |
| | 0.1 | 1.078 | 1.311 | 1.083 | 1.318 | 1.087 | 1.322 | 1.116 | 1.355 | 1.145 | 1.406 | 1.169 | 1.452 |
| | 0.2 | 1.157 | 1.374 | 1.161 | 1.380 | 1.169 | 1.388 | 1.207 | 1.420 | 1.240 | 1.470 | 1.268 | 1.513 |
| | 0.5 | 1.515 | 1.752 | 1.536 | 1.787 | 1.571 | 1.833 | 1.732 | 1.993 | 1.944 | 2.243 | 2.124 | 2.448 |
| | 0.8 | 2.031 | 2.498 | 2.098 | 2.663 | 2.196 | 2.832 | 2.749 | 3.528 | 3.623 | 4.603 | 4.378 | 5.491 |
| | 1.0 | 2.475 | 3.286 | 2.578 | 3.585 | 2.749 | 3.931 | 3.790 | 5.340 | 5.523 | 7.514 | 7.026 | 9.311 |
| 0.4 | 0.0 | 1.073 | 1.173 | 1.077 | 1.177 | 1.082 | 1.183 | 1.130 | 1.244 | 1.201 | 1.314 | 1.254 | 1.365 |
| | 0.1 | 1.094 | 1.196 | 1.097 | 1.201 | 1.104 | 1.206 | 1.161 | 1.267 | 1.233 | 1.343 | 1.289 | 1.398 |
| | 0.2 | 1.131 | 1.241 | 1.135 | 1.246 | 1.147 | 1.257 | 1.227 | 1.337 | 1.306 | 1.417 | 1.375 | 1.488 |
| | 0.5 | 1.317 | 1.488 | 1.339 | 1.521 | 1.378 | 1.567 | 1.577 | 1.749 | 1.865 | 2.072 | 2.117 | 2.349 |
| | 0.8 | 1.636 | 1.985 | 1.691 | 2.069 | 1.780 | 2.198 | 2.318 | 2.781 | 3.239 | 3.816 | 4.066 | 4.723 |
| | 1.0 | 1.941 | 2.504 | 2.015 | 2.638 | 2.167 | 2.861 | 3.111 | 3.972 | 4.813 | 5.875 | 6.355 | 7.559 |
| 0.5 | 0.0 | 1.086 | 1.158 | 1.090 | 1.160 | 1.097 | 1.165 | 1.150 | 1.220 | 1.235 | 1.302 | 1.308 | 1.381 |
| | 0.1 | 1.102 | 1.179 | 1.106 | 1.180 | 1.113 | 1.185 | 1.178 | 1.245 | 1.271 | 1.339 | 1.350 | 1.424 |
| | 0.2 | 1.130 | 1.211 | 1.134 | 1.217 | 1.147 | 1.228 | 1.238 | 1.310 | 1.345 | 1.417 | 1.439 | 1.511 |
| | 0.5 | 1.272 | 1.414 | 1.294 | 1.446 | 1.335 | 1.492 | 1.550 | 1.684 | 1.879 | 2.045 | 2.161 | 2.355 |
| | 0.8 | 1.546 | 1.827 | 1.596 | 1.899 | 1.684 | 2.018 | 2.224 | 2.574 | 3.169 | 3.609 | 4.010 | 4.516 |
| | 1.0 | 1.801 | 2.260 | 1.871 | 2.368 | 2.021 | 2.558 | 2.931 | 3.568 | 4.595 | 5.380 | 6.163 | 7.059 |
| 1.0 | 0.0 | 1.138 | 1.138 | 1.142 | 1.141 | 1.145 | 1.144 | 1.236 | 1.192 | 1.416 | 1.343 | 1.601 | 1.523 |
| | 0.1 | 1.141 | 1.142 | 1.144 | 1.144 | 1.154 | 1.152 | 1.261 | 1.220 | 1.470 | 1.399 | 1.683 | 1.609 |
| | 0.2 | 1.144 | 1.145 | 1.152 | 1.154 | 1.172 | 1.172 | 1.309 | 1.267 | 1.565 | 1.486 | 1.801 | 1.685 |
| | 0.5 | 1.198 | 1.232 | 1.220 | 1.261 | 1.267 | 1.309 | 1.547 | 1.547 | 2.075 | 2.056 | 2.555 | 2.514 |
| | 0.8 | 1.364 | 1.413 | 1.399 | 1.470 | 1.486 | 1.565 | 2.056 | 2.075 | 3.171 | 3.171 | 4.196 | 4.162 |
| | 1.0 | 1.481 | 1.615 | 1.545 | 1.686 | 1.685 | 1.801 | 2.514 | 2.555 | 4.162 | 4.190 | 5.977 | 5.977 |

← 301

SYSTEM AND METHOD FOR DETERMINING DIRECT DAMAGE TOLERANCE ALLOWABLES

TECHNICAL FIELD

The embodiments of the present disclosure relate to determining damage tolerance allowables for a structure, such as an aircraft structure.

DESCRIPTION OF RELATED ART

Conventional method of determining damage tolerance allowables for aircraft structure can include multiple steps of approximations and derivations that have conservatism and variability, which can result in the designing of aircraft structures with too much conservatism, thus being heavier than actually necessary. A conventional method of calculating damage tolerance allowables is outlined in ASTM E647.

There is a need for an improved method of calculating damage tolerance allowables.

DESCRIPTION OF THE DRAWINGS

The novel features believed characteristic of the system and method of the present disclosure are set forth in the appended claims. However, the system and method itself, as well as a preferred mode of use, and further objectives and advantages thereof, will best be understood by reference to the following detailed description when read in conjunction with the accompanying drawings, wherein:

FIG. 1 is a side view of a rotorcraft, according to one example embodiment;

FIG. 2 is a schematic view of a method of determining damage tolerance allowables, according to one example embodiment;

FIG. 3 is a table, according to one example embodiment;

FIG. 4 is a schematic view of a method of manufacturing a part, according to one example embodiment;

DESCRIPTION OF THE PREFERRED EMBODIMENT

Figure 5:
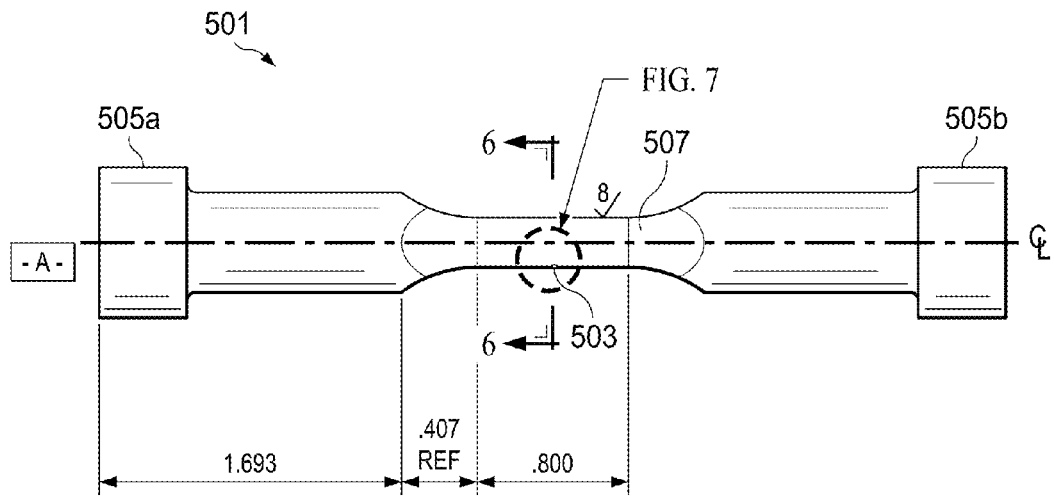
FIG. 5 is a side view of a specimen, according to one example embodiment.
Figure 6:
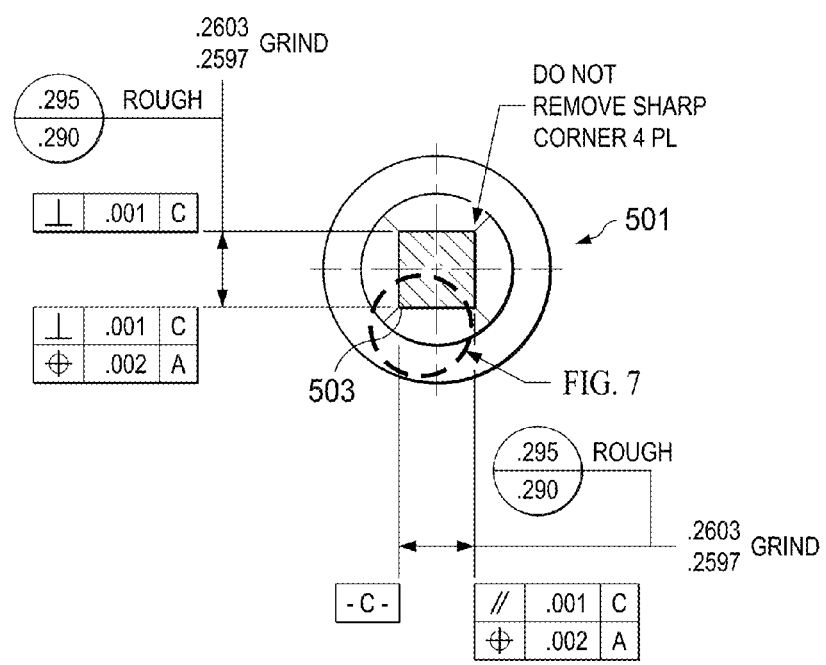
FIG. 6 is a cross-section view take at section lines 6-6 in FIG. 5, according to one example embodiment.

Illustrative embodiments of the system and method of the present disclosure are described below. In the interest of clarity, all features of an actual implementation may not be described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present disclosure, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Damage tolerance allowables are essential for the damage tolerance design of rotorcraft structures, such as dynamic parts. When an aircraft is designed to certain usage and load conditions, the combination of those conditions flow down to the structures and translate into a certain stress level that depends upon the material composition of the parts and the detail design of the parts. A comparison of that stress level of the part to the damage tolerance allowables determines whether the part can satisfy the damage tolerance requirements with the particular design. If the stress level exceeds the damage tolerance allowables, the part requires re-design to reduce the stress level of the part, which typically causes an increase in the weight of the part or a decrease in the overall load and usage capability of the aircraft.

If the damage tolerance allowables are overly conservative, the stress level of the part would have to be designed to meet the overly conservative damage tolerance criteria, which would cause the size (and weight) of the part to increase to meet the given usage and load requirements of the aircraft. Alternatively, the usage and load capabilities of the aircraft would need to be lowered to maintain any weight requirements.

Conventional ideology of determining damage tolerance requirements includes introduction of a crack in a critical location of a structure and analyzing the growth of that crack due to the aircraft usage and loading. Conventionally, in order to satisfy damage tolerance requirements for high stress high frequency loaded rotorcraft structures, the initial crack must not be allowed to grow. The term that describes this "no growth" phenomena is called "threshold value." Since the threshold values for small cracks were difficult to determine in the laboratory, the conventional method (ASTM E647) determines threshold values obtained by testing the long crack growth under decreasing loading until the crack stops growing. Based on threshold values obtained in such approximate ways, the small crack no-growth damage tolerance allowables are derived with further approximations and knockdowns. Multiple steps of approximations and derivations result in conservatism and variability, thus generating overly conservative damage tolerance allowables.

The present disclosure includes methods and systems of generating no-growth damage tolerance allowables for structures, which allow for higher stress level in the damage tolerant designed part with less weight while meeting the usage and load requirements of the aircraft. Certain embodiments include methods and systems of directly obtaining no-growth damage tolerance allowables for aircraft structure, the allowables being approximately 15%-30% higher than allowables produced by the conventional ASTM E647 method. Moreover, a 15%-30% higher allowable can equate to an approximately 15%-30% weight savings of the aircraft structure. Furthermore, certain embodiments of the methods and systems of directly obtaining no-growth damage tolerance allowables for aircraft structure may prevent the necessity of full scale aircraft structure testing that may otherwise be required for certification. The method of the present application is a coupon specimen testing method that generates threshold stress data for fatigue crack initiation in a metallic material. In one embodiment, "threshold" can be the fatigue stress state {mean stress, oscillatory stress}, below which a flaw or a crack in a metallic material will not grow. As such, threshold stress may also be called "no-growth threshold."

In one embodiment, the test method generates threshold stress data for crack initiation. The test specimen can be a square-bar coupon, cyclically loaded along the axis. Each coupon specimen contains a notch at a corner of the center-plane of the specimen to simulate a flaw.

Figure 23:
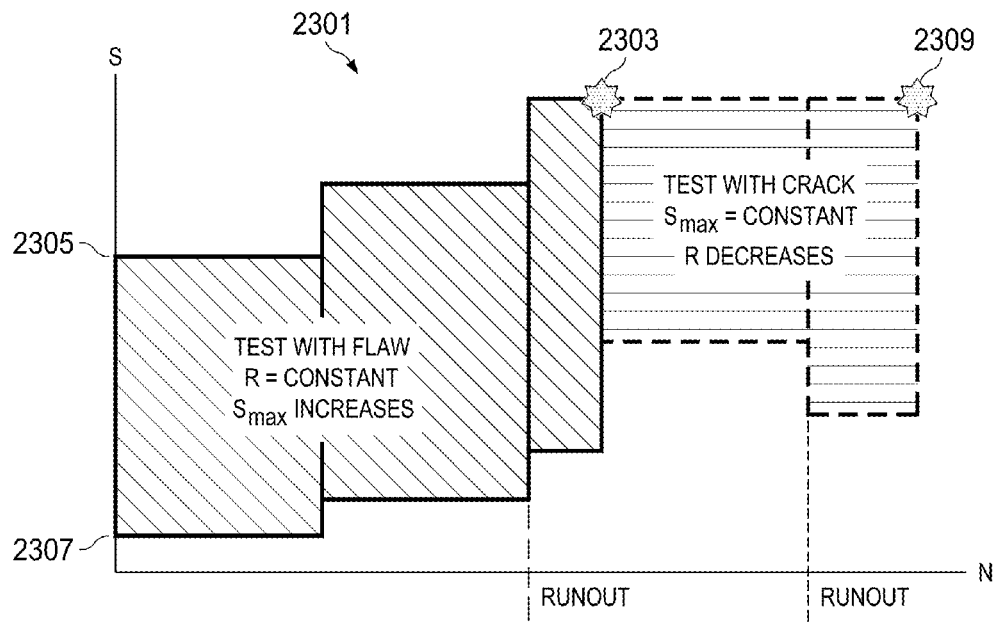
FIG. 23 is a graphical representation of a testing method, according to one example embodiment.

Referring to FIG. 23, a graphic 2301 illustrates how the method derives the threshold stress. The test starts at required stress ratio R with an initial load max 2305 and initial load min 2307. If crack initiation occurs and the criterion $\Delta a_o/\Delta N \leq 4 \times 10^{-9}$ in/cycle is met, this load is the threshold fatigue load, from which the threshold stress of the material can be obtained. Otherwise if with that load the number of cycle reaches $N_0 = 1,000,000$ without crack initiation, the load will be bumped up to a higher level and the test will be repeated. The number of 1,000,000 cycles can be chosen because it meets the threshold criterion with the maximum presumed crack initiation (0.004-in) even if it does not happen. This way the necessary conservatism of the data is ensured. This process can be repeated until crack initiation occurs at an occurrence 2303 and the threshold criterion is not met. In this case, the previous load level will be used for no-growth threshold stress of the flaw.

Once the crack initiation occurs at the occurrence 2303, the testing continues and turns into determination of threshold stress for a crack, which becomes evident by a crack growth occurrence 2309. The testing maintains the last maximum load for the test with the flaw to avoid overload effect, but changes the minimum load. The same process as testing with flaw is used and may need to be repeated until the threshold stress is achieved for the crack.

Figure 24:
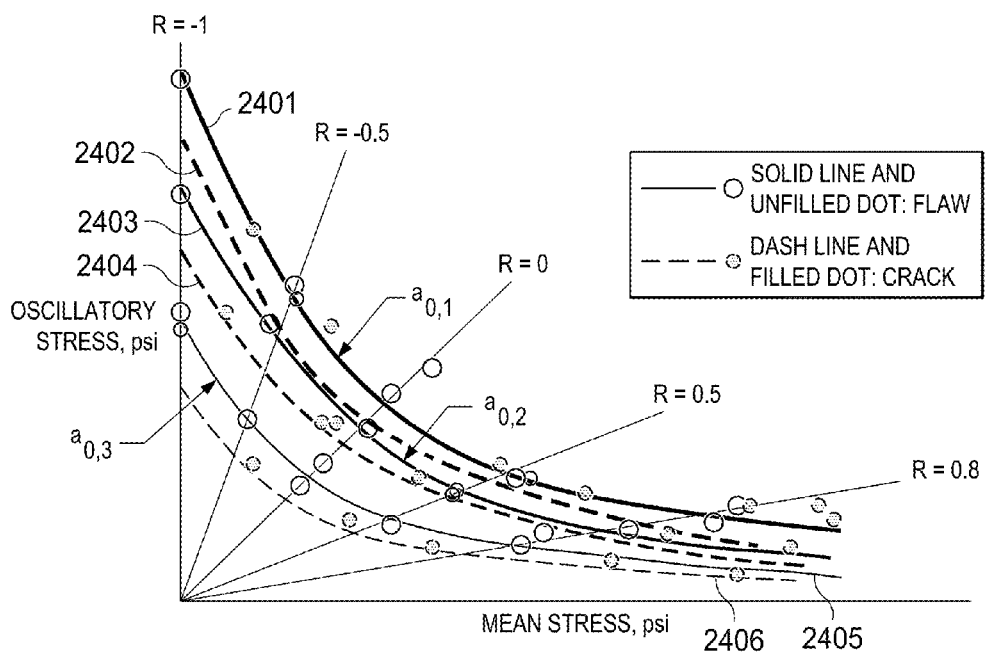
FIG. 24 is a graphical representation of threshold stress data, according to one example embodiment.

Referring now also to FIG. 24, the tests can be performed with various stress ratios R for the coupons of same notch size $a_0$, which together generate a threshold stress curves $\{S_{mean}, S_{osc}\}$ for notch length $a_{0,1}$. In same way, the threshold stress curves can be achieved for various flaw sizes, shown as solid lines 2401, 2403, 2405 in FIG. 24. Similarly, the data obtained for various crack lengths can also form the threshold stress curves for no-growth of crack(s), shown as dotted lines 2402, 2404, 2406 in FIG. 24. Regarding FIG. 24, exemplary threshold stress data generated via the test method is illustrated, wherein $(a_{0,1} < a_{0,2} < a_{0,3})$.

Referring now to FIG. 1 in the drawings, a rotorcraft 101 is illustrated. Rotorcraft 101 can have a rotor system 103 with a plurality of rotor blades 105. The pitch of each rotor blade 105 can be manipulated in order to selectively control direction, thrust, and lift of rotorcraft 101. Rotorcraft 101 can further include a fuselage 107, anti-torque system 109, and an empennage 111. The structure of rotorcraft 101 can include a variety of airframe structures, such as bulkheads, ribs, longerons, stringers, keels, skins, spars, to name a few examples. A bulkhead 113 is labeled for illustrative purposes.

The methods and systems of the present disclosure relate to determining damage tolerance ("DT") allowables for a structure, such as an aircraft structure. It should be appreciated that rotorcraft 101 is merely illustrated as one of many different types of aircraft whose structure can be analyzed and designed using the methods and systems of the present disclosure. Furthermore, other aircraft can include, fixed wing aircraft, hybrid aircraft, unmanned aircraft, tiltrotor aircraft, to name a few examples.

Referring now also to FIG. 2, a method 201 of directly determining damage tolerance allowables is schematically illustrated. In one embodiment, method 201 is a test method for determining no-growth threshold stress for a flaw or a crack in a metallic component. Applicable metals can include aluminum, titanium, and steel, to name a few examples. The conventional ASTM E647 method derives crack growth threshold ($\Delta K_{TH}$) from the derived crack growth rate curve (da/dN vs. $\Delta K$) that is based on crack growth testing a-N data, where K is stress intensity factor (SIF). Once $\Delta K_{TH}$ is derived, it is further converted into no-growth threshold fatigue stress. As a contrast, the direct test method 201 can generate a fatigue stress data in which a flaw or a crack will not grow. In this way, the no-growth damage tolerance allowables can be determined based on the directly obtained fatigue test stress data.

Method 201 can include a step 203 of preparing a specimen, a step 205 of calculating an initial load, a step 207 of testing the specimen, and a step 209 of processing data. Each of these steps are described in further detail herein.

Alternating or Oscillatory Stress ($\sigma_{osc}$): The alternating stress is one half of the stress range during a stress cycle.

Maximum Stress ($\sigma_{max}$): The highest algebraic value of stress in the stress cycle, tensile stress being considered positive and compressive stress negative.

Mean Stress (Steady Stress, $\sigma_{mean}$): The algebraic mean of the maximum and minimum stress in one stress cycle. A tensile stress is considered positive.

Minimum Stress ($\sigma_{min}$): The lowest algebraic value of the stress in the stress cycle.

Scatter: This term usually refers to the scatter of test points which define a $\sigma_{osc}$-$\sigma_{mean}$ curve.

Stress Cycle (N): A stress cycle is the smallest section of the stress-time function which can be repeated periodically and identically.

Stress Ratio (R): The ratio of minimum stress divided by maximum stress.

Crack Initiation: In one example embodiment, crack initiation is when a pre-crack appears beyond 0.001-inch but shorter than 0.004-inch ($0.001\text{-inch} \le \Delta c_{i,o} \le 0.004\text{-inch}$), indicated by the potential drop method (PDM) during testing. i=1, 2, the two sides of gauge of the corner crack test coupon on which notch (and crack) can be observed.

Initial Flaw Size ($c_{i,o}$): Initial flaw size is defined as one of the design requirements for a DT part in which a flaw of the initial flaw size does not grow.

Initial Crack Size ($c_{i,c}$): In one example embodiment, the initial crack size is the size of crack initiation.

Crack Growth Increment ($\Delta c_i$): In one example embodiment, the crack growth increment is the length of crack initiation.

Initial Load ($P_o$): A load the test starts with.

Final Load ($P_C$): The load at which the notch starts to grow.

Test and Testing Block: A Test is an iterating process of stepped load with one time set up of testing frame. In one example embodiment, a Testing Block is counted as a 1,000,000 cycle run of fatigue test except the last block for which the flaw/crack starts to grow before it reaches the 1,000,000 cycles.

PD or PDM: Potential drop or potential drop method. A method to indicate occurrence of crack growth by monitoring voltage change of a special detection system.

Referring now also to FIGS. 5-8, a specimen 501 which can also be referred to herein as "Ks Bar", is illustrated. In one example embodiment, specimen 501 is a bar coupon for an axially loaded fatigue test that has a gauge of square cross-section and a corner notch 503 on the middle plane of the specimen 501. As shown in FIG. 5, the specimen 501 is symmetric about a center-plane.

Method 201 generates crack initiation data with using one or more specimens 501, each with a corner notch 503 at the center-plane of the specimen 501. In one implementation, three notch sizes can be utilized. Example nominal notch sizes for general metal-forming materials are 0.005-inch, 0.010-inch, and 0.015-inch, measured on each side of the corner of the specimen 501. Example nominal notch sizes for casting materials are 0.015-inch, 0.025-inch, and 0.050-inch, also measured on each side of the specimen 501. For each notch size, twelve coupons can be used to support the tests at five stress ratios, viz. R=-1, -0.5, 0.05, 0.5, 0.8. Among these five stress ratios, R=0.05 is primary and at least four specimens 501 can be used to support the R=0.05 tests. For the other four stress ratio tests, at least two specimens 501 can be used for each stress ratio tests. Table 1 lists an example specimen matrix for the requirements of test specimens, i.e., thirty-six coupons. In addition, four un-notched spare specimens 501 can be used to mitigate unexpected events, resulting in a total of forty coupons that can be used in the example test program. It should be appreciated that the exact quantity of specimens 501 used in method 501 is implementation specific; furthermore, the quantity of specimens 501 described herein are for exemplary purposes and are not intended to be restrictive.

TABLE 1

Specimen Matrix

| $c_{i,o}$ (in) | | Stress Ratio | | | | | | |
|---|---|---|---|---|---|---|---|---|
| | | -1 | -0.5 | 0.05 | 0.5 | 0.8 | | |
| Wrought | Casting | | | Specimen Number | | | Total | |
| 0.005 | 0.015 | | | | | | TBD | |
| 0.010 | 0.025 | | | | | | TBD | |
| 0.015 | 0.050 | | | | | | TBD | Spare |
| | | | | | | | TBD | TBD |
| | | | | | | | Total | TBD |

Depending on the probable flaw (or crack) orientation in a structural part for which the threshold stress data of the material is desired, the specimen 501 is machined from the material direction so that the corner notch 503 of the specimen 501 is of the same material orientation as in the structural part.

For instance, a probable flaw in the S-T (or R-C) material orientation is possible in a structural part and no-growth threshold stress data is needed. For wrought materials, the axial direction of the specimen 501 can align with the thickness direction if it is made from a thick plate, or can align with the radius direction if it is made from a round bar. With this alignment, the corner notch 503 of a specimen 501 is in the S-T or R-C orientation. There may not be a specific requirement on alignment of the specimen 501 with respect to the sand casting material since the grain direction is not significant in such a case. The length of the specimen 501 can be any implementation specific length; however, one example length is approximately four inches. Another example length is five inches. The head buttons 505a and 505b of the specimen 501 are designed for the axial load application, for which the perpendicularity of the shoulders to the axis of the specimen 501 is desired during the test.

Figure 7:
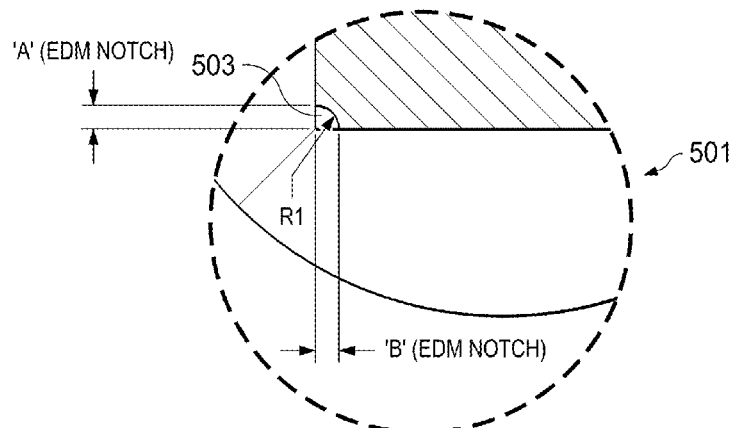
FIG. 7 is a detail view taken from FIG. 6, according to one example embodiment.
Figure 8:
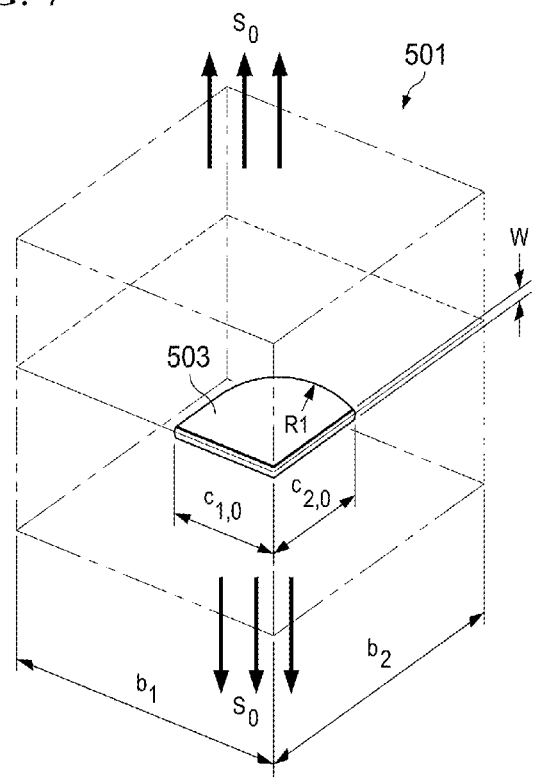
FIG. 8 is a stylized perspective view of a specimen, according to one example embodiment.

In the example embodiment, a gauge section 507 is of square cross-section. The center cross-section of the gauge section 507 is the mid-plane (also symmetric plane) of the specimen 507, on which a notch 503 is induced at a corner, as shown at least in FIGS. 7 and 8. In one example embodiment, the nominal dimensions of corner notch 503 is $c_{i,o}$=0.05, 0.010, or 0.015 for metal-forming materials and 0.015, 0.025, or 0.050 for casting materials, where i=1 (Side 1) and 2 (Side 2), measured from the corner point of the specimen 501 to the tip of the notch 503 on each side of the gauge, as shown in FIG. 8. In one example embodiment, the width W of the corner notch 503 is 0.003-inch. It is desired that the bottom of the corner notch 503 (also called notch front) have a curved portion R1 as shown in FIGS. 7 and 8.

The material of the specimen 501 should be the same as the material as the structural part of which the damage tolerance allowables are being determined. For example, the material of the specimen 501 should not only be of the same material, but also have the same material conditions, such as ultimate tensile strength (UTS), heat-treatment, hardening condition, and material form, as the structural part of which the damage tolerance allowables are being determined.

In one example embodiment, notch 503 is generated using an electrical discharge machining (EDM) method; however, it should be appreciated that other methods of creating notch 503 may be used, such as sawing, broaching, or milling, for example, as long as notch can be created with a curved portion R1.

Figure 19:
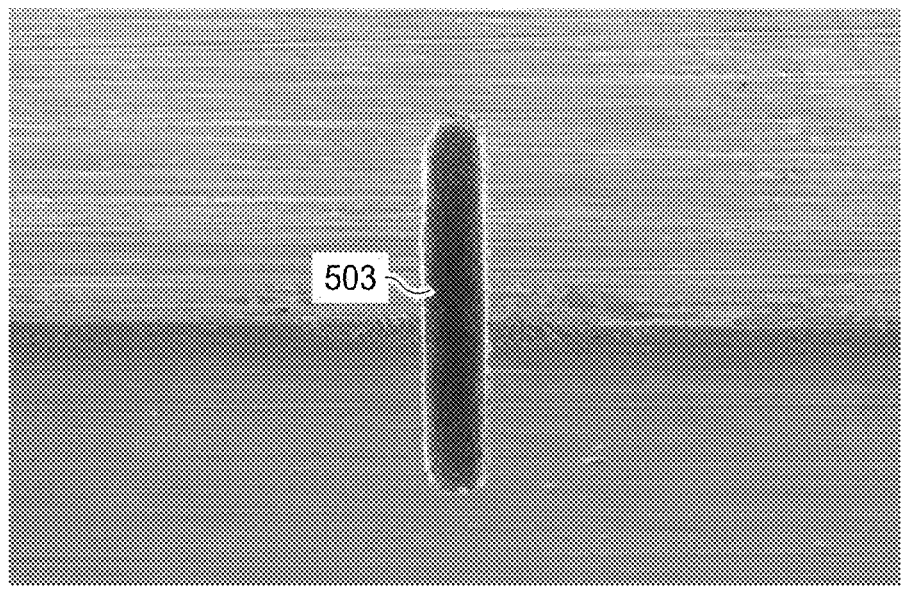
FIG. 19 a view of an EMD corner notch, according to one example embodiment.
Figure 20:
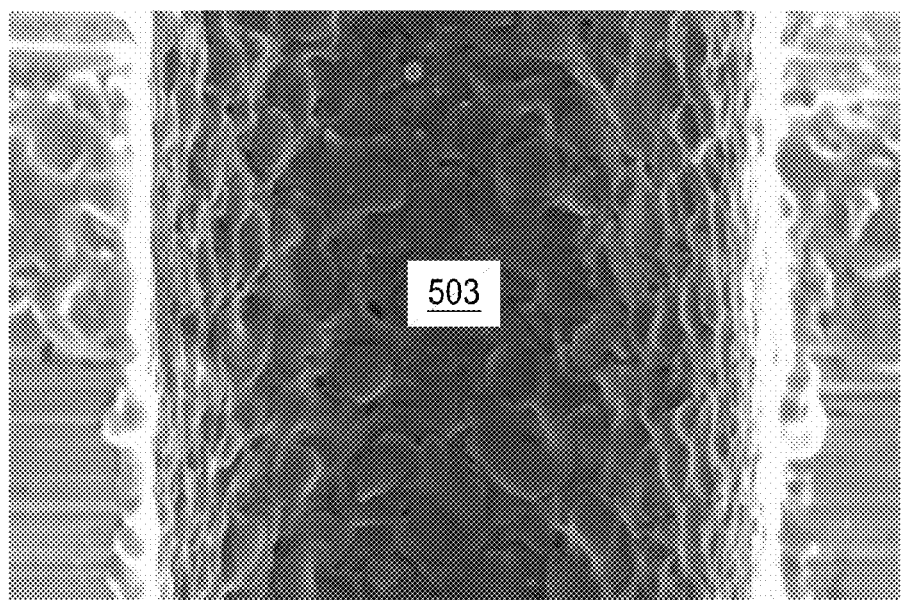
FIG. 20 a close up view of an EMD corner notch before chemical modification, according to one example embodiment.
Figure 21:
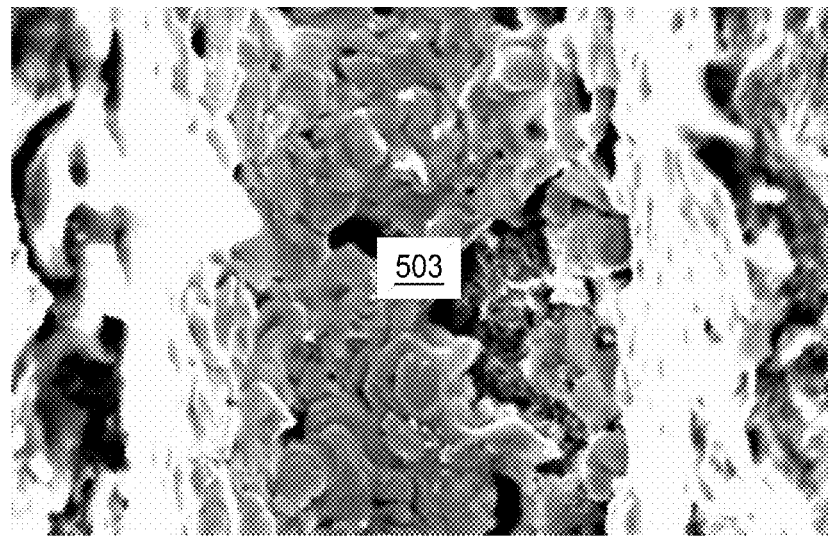
FIG. 21 a close up view of an EMD corner notch after chemical modification, according to one example embodiment.

Referring to FIGS. 19-22, a portion of notch 503 is metallurgically depicted. A post-notching chemical treatment can be desirable to modify the EDM corner notch of the specimen 501. One purpose of the etching process is to remove re-melt material layer of high hardness along a notch surface 505 of the notch 503. The re-melt material layer can be caused by high temperature of electric discharge during the notching process. Another important purpose of the post-notching treatment is to weaken the grain bonds along the notch surface 505 of notch 503 to make the evaluation more conservative. FIG. 19 shows an example of a corner notch 503 produced with an EMD process. FIG. 20 is a close-up view of a front of the notch 503 before chemical modification. FIG. 21 is a close-up view of a front of the notch 503 after chemical modification. A comparison between FIGS. 20 and 21 reveals that the re-melt layer has been disintegrated and separated from a root notch 509 of notch 503 after the treatment. This results in a desired notch severity (worst notch) for the test.

Figure 22:
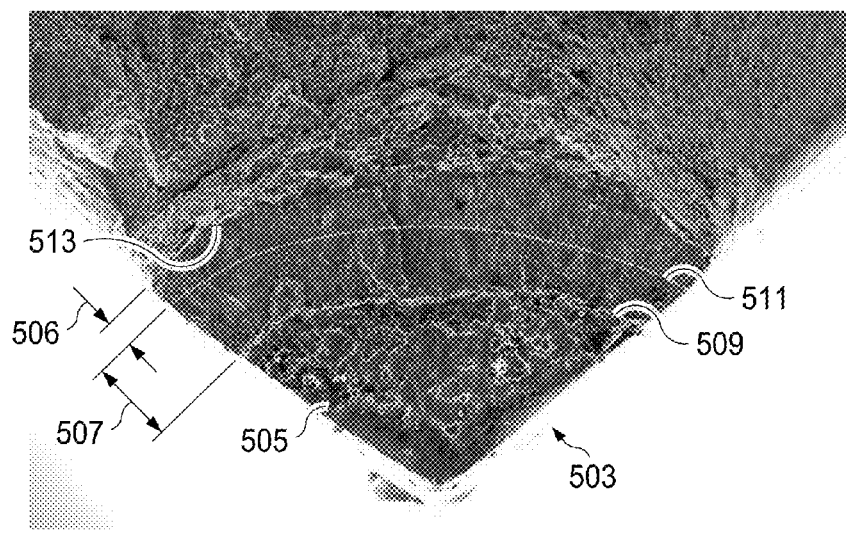
FIG. 22 a close up cross-sectional view of a notch front and crack front after chemical modification, according to one example embodiment.

FIG. 22 illustrates the notch 503 in a specimen 501 that has been sectioned at the crack plane after testing. Such a sectioning of specimens 501 can be performed to verify notch measurements and crack measurements using a scanning electron microscope (SEM) measurement, for example. Creation and etching of the notch 505 results in a notch root 509. During testing, a first crack 507 is created, which exists between notch root 509 and a first crack front 511. As discussed further herein, the test is temporarily halted upon detection of the first crack 511. The test can be resumed until a second crack 506 is created between first crack front 511 and a second crack front 513.

Figure 9:
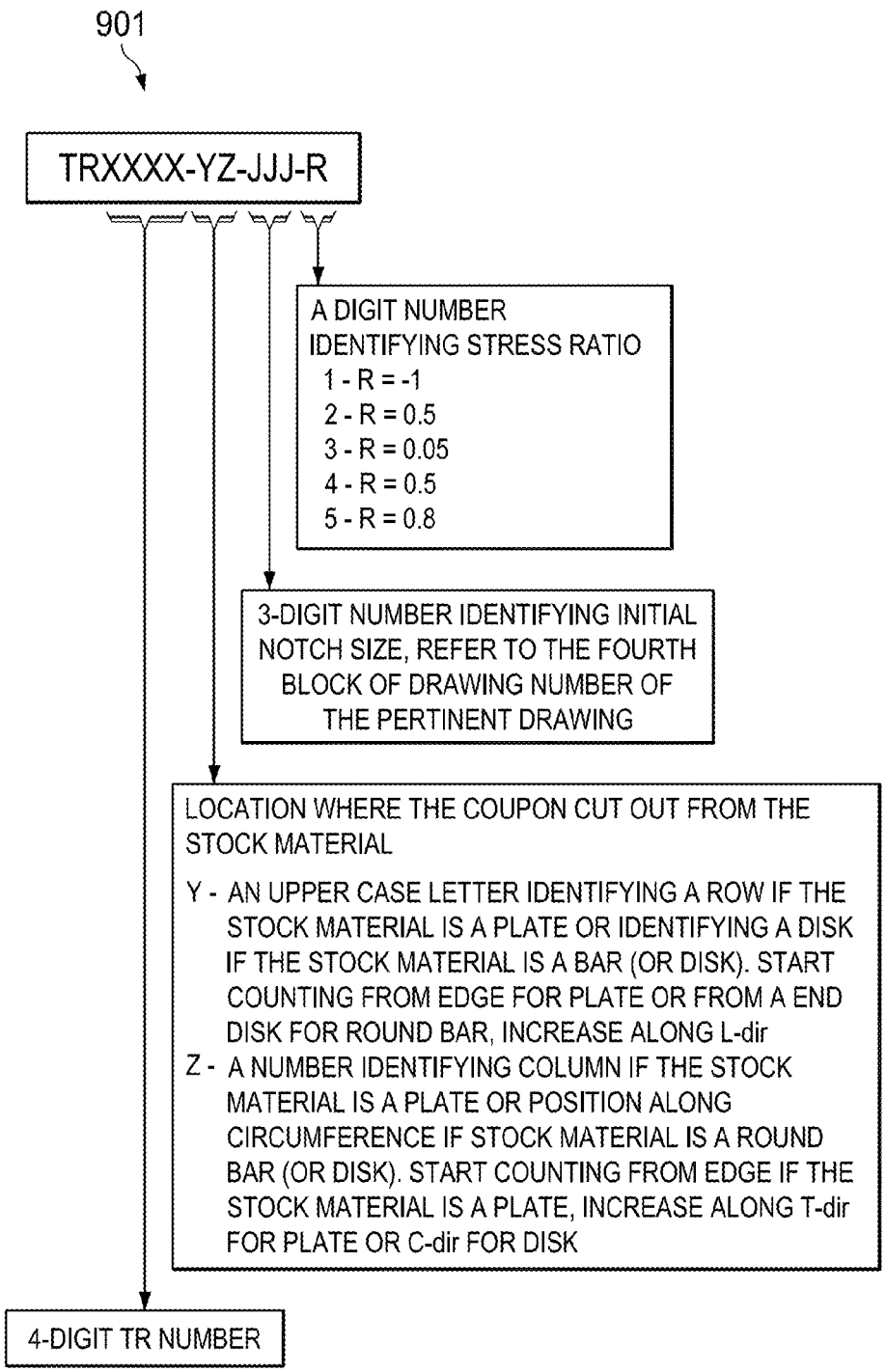
FIG. 9 is an illustrative specimen ID for a specimen, according to one example embodiment.

Now referring to FIG. 9, an exemplary specimen ID 901 can be utilized to mark each specimen 901 to keep track of critical information and insure accurate test data. The specimen ID 901 can include information such as: Test Request (TR) number, the location that specimen blank is cut out from the stock material, the notch size, and the stress ratio at which the coupon will be tested, as illustrated in FIG. 9.

Figure 10:
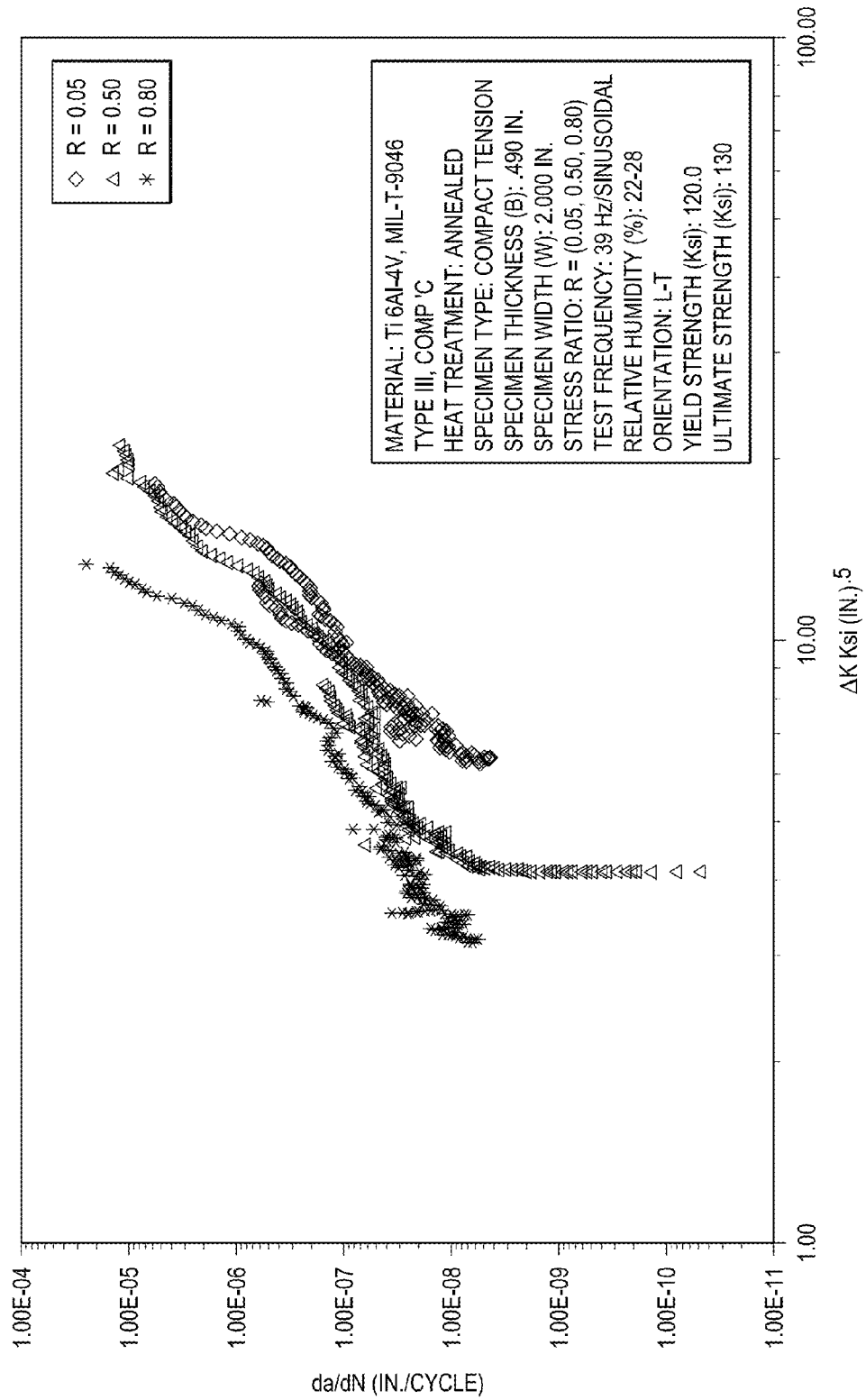
FIG. 10 is an illustrative da/dN vs. ΔK curve, according to one example embodiment.

Referring again to FIG. 2, method 201 further includes a step 205 of calculating an initial load. The step 207 of testing the specimen(s) 501 is an iterative process that starts with an initial load to converge the load to the point at which the flaw starts to grow. A reference da/dN vs. $\Delta K$ curve is preferred to narrow the range for the initial load determination. The reference information can be an existing $\Delta K_{TH}$ data or a plot of da/dN vs. $\Delta K$ curves referred for the material to be tested or for the materials that have characteristics similar to that to be tested. These characteristics include the chemical elements of the material, ultimate tensile strength (UTS), material form, and material treatments. FIG. 10 is an example of a da/dN vs. $\Delta K$ curve 1001 for Ti-6Al-4V.

Step 205 can further include using a stress intensity factor (SIF) to calculate the initial load. SIF equations for a corner notch (crack) of a square bar can be used in the initial load calculation. In one example embodiment, a correction factor can be used to account for geometrical effects on SIF. FIG. 8 depicts geometries and loading application for the test procedure. Table 2 lists the notations of FIG. 8 and the associated descriptions.

TABLE 2

Specimen Matrix

| Symbol | Description |
| --- | --- |
| $b_1$ | Width of the cross-section on the side of the gauge aligning with L-direction |
| $b_2$ | Width of the cross section on the side of the gauge align with T-direction |
| $S_0$ | Magnitude of uniform remote stress |
| $c_1$ | Crack length measured on the side aligning with L-direction of the gauge |
| $c_2$ | Crack length measured on the side aligning with T direction of the gauge |

Method 201 is an iterative process which can include an interval of cycles, such as 1,000,000 cycles for example, for each step of iteration until a flaw (or a crack) starts to grow. In order to determine the load at which a flaw starts to grow, the test starts with an initial load and iterates with the calculated load increments until the flaw grows. The initial load can be determined based on the reference threshold $\Delta K_{TH}$ for stress ratio $R_0 = 0$ and the traditional A=0.8 approximation for differentiated stress ratio $R_j$. Starting with the reference $\Delta K_{TH}$, Equations 1-8 are the basis to determine initial load from stress intensity factor (SIF) for a corner crack initiation test. By re-arranging Equation 1, with the support of Equations 2-8 and Table 3, the remote stress $S_0$ can be calculated. Multiplying $S_0$ by area of gauge cross-section, the initial load can be determined.

$$K = F_0 S_0 \sqrt{\pi c} \quad (1)$$

$$F_0 = f_x f_\phi f_a f_0 \quad (2)$$

$$f_x = \left[1 + 1.464\left(\frac{c1}{c2}\right)^{1.65}\right]^{-\frac{1}{2}}, \quad \text{for } \frac{c1}{c2} \leq 1 \quad (3)$$

$$f_x = \left[1 + 1.464\left(\frac{c2}{c1}\right)^{1.65}\right]^{-\frac{1}{2}}, \quad \text{for } \frac{c1}{c2} > 1 \quad (4)$$

$$f_\phi = \left[\left(\frac{c1}{c2}\cos\phi\right)^2 + \sin^2\phi\right]^{\frac{1}{4}}, \quad \text{for } \frac{c1}{c2} \leq 1 \quad (5)$$

$$f_\phi = \left[\cos^2\phi + \left(\frac{c2}{c1}\sin\phi\right)^2\right]^{\frac{1}{4}}, \quad \text{for } \frac{c1}{c2} > 1 \quad (6)$$

$\phi = 0°$ at $c_2$-tip,
$\phi = 90°$ at $c_1$-tip $$f_a = 1, \quad \text{for } \frac{c1}{c2} \leq 1 \quad (7)$$

$$f_a = \sqrt{\frac{c2}{c1}}, \quad \text{for } \frac{c1}{c2} > 1 \quad (8)$$

$f_0$=Tabular data (Table 301 in FIG. 3)

Referring again to FIG. 2, method 201 further includes a step 207 of testing the specimen(s) 501. Step 207 includes iteratively loading a specimen 501 at stepped loads for an implementation specific number of cycles until a flaw (or a crack) starts to grow in corner notch 503. The test process in step 207 starts with an Initial Load ($P_0$) and ends at the Final Load ($P_C$) at which the flaw (or crack) starts to grow. Each test determines the Final Load, Mean Stress, and Oscillatory Stress for the given flaw size, stress ratio, and limited cycles.

Figure 11:
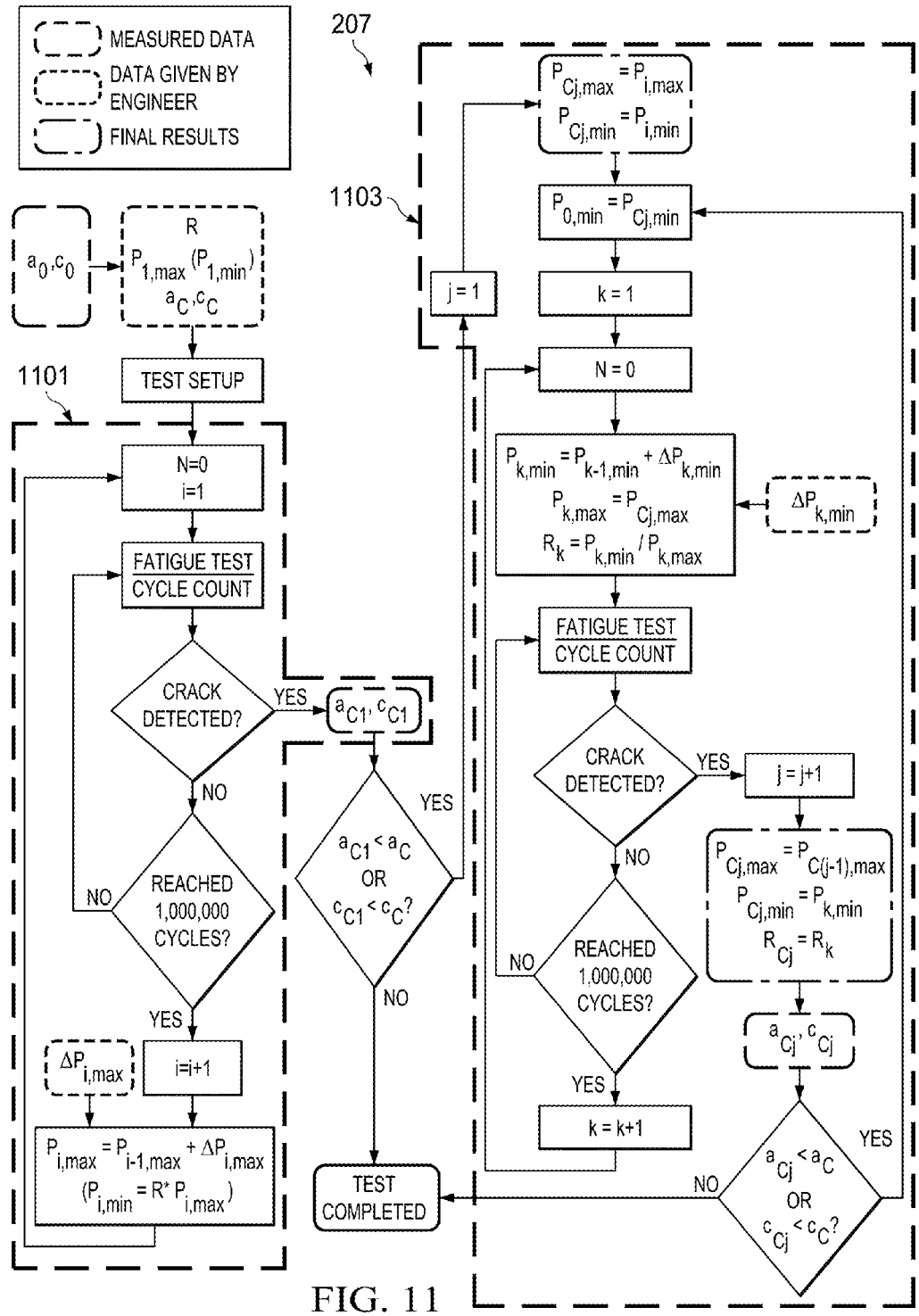
FIG. 11 is a schematic view of a process of testing a specimen, according to one example embodiment.

Referring also to FIG. 11, pretest data can include: 1) gauge section dimensions t and W (measurements), 2) notch dimensions $a_0$, $c_0$, and b, where b is the width of the notch (measurements), 3) stress ratio R, 4) Initial Load $P_1$, 5) final crack length $a_c$ and $c_c$, 6) testing frequency, and 7) lab temperature (recorded by the testing lab), and 8) lab humidity (recorded by the testing lab).

After entering any pretest data, the testing step 207 can further include: installing the specimen 501, tuning for alignment, calibrating the measurement and data acquisition system, setting $P_{max}$ and $P_{min}$ for cyclic load, setting potential drop (PD) using a needle-spring method.

Figure 12:
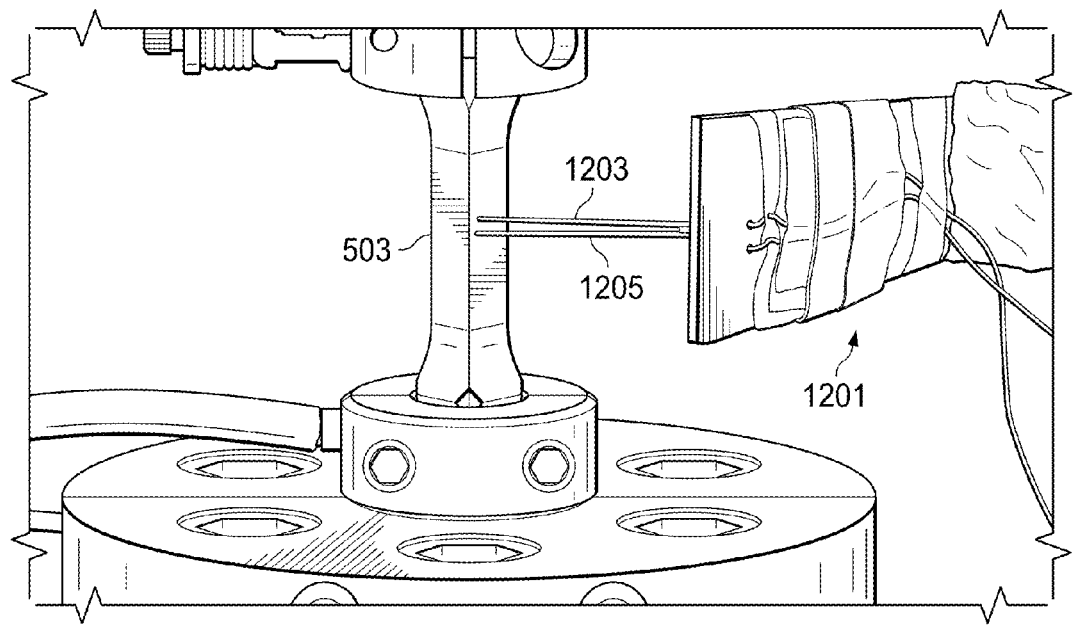
FIG. 12 is a perspective view of a test setup that uses a potential drop (PD) to determine an occurrence of crack growth, according to one example embodiment.

Referring also to FIG. 12, a specimen 501 is illustrated installed in a test setup. A first needle 1203 and a second needled 1205 are pressed against either side of the notch 503. During testing, a current is passed through the notch 502 between needles 1203 and 1205. The detection of crack growth is a result of a change in electrical resistance between needles 1203 and 1205. The utilization of needles 1203 and 1205 in a PD system 1201 prevents the need for welding or otherwise attaching sensors that could prove an undesired cracking or annealing of the specimen 501. In one example embodiment, the PD system 2101 is set such that the test stops when $\Delta a = (0.001 \sim 0.004)$ inch, for example. In one example embodiment, the cycle count (N) is set to zero prior to the start of a test block, and the maximum cycle number is set to 1,000,000 for a testing block such that the test stops at N=1,000,000 if no $\Delta a$ is detected.

Referring again to FIG. 11, step 207 of method 201 is illustrated in a block diagram format. Step 207 can be broken down between a constant R testing loop 1101 and a constant $P_{max}$ testing loop 1103. Each of the constant R testing loop 1101 and a constant $P_{max}$ testing loop 1103 are discussed further herein.

Figure 13:
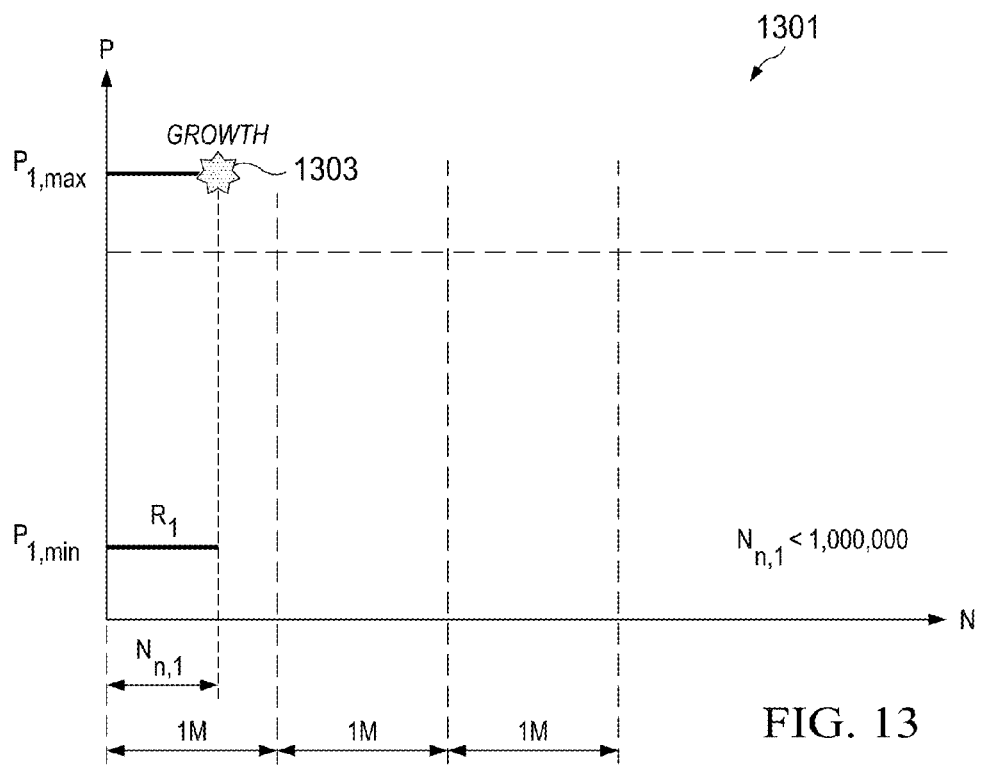
FIG. 13 is a graph, according to one example embodiment.
Figure 14:
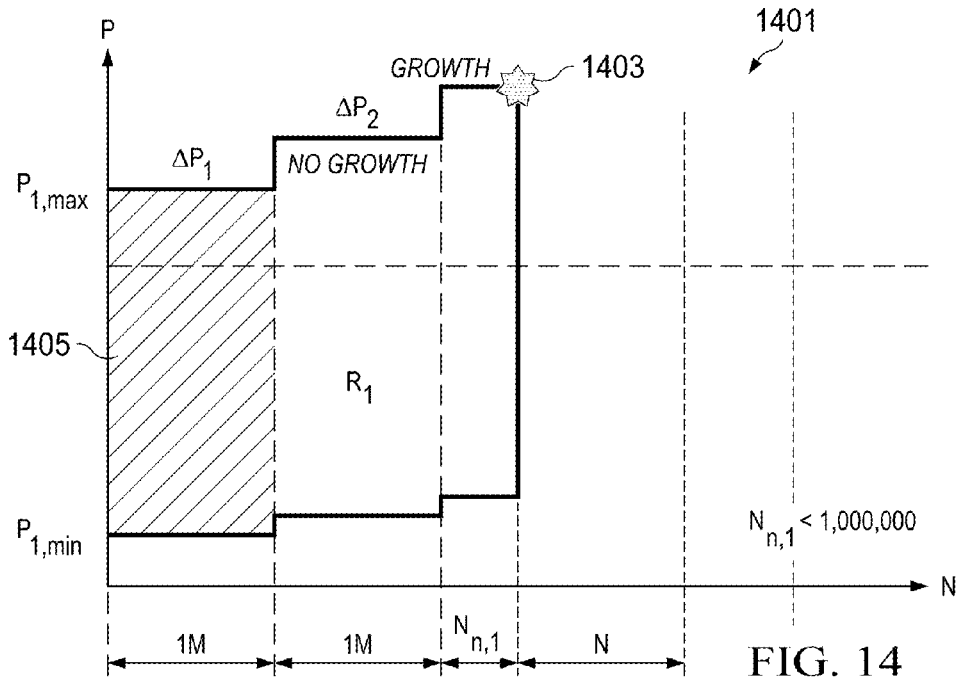
FIG. 14 is a graph, according to one example embodiment.

The constant R testing loop 1101 can include starting the test with the PD 1201 turned on and cycle count on. If a crack extension is detected via the PD 1201, the test is stopped, as shown in graph 1301 of FIG. 13. In the illustrated graph 1301, a crack extension is detected at occurrence 1303, which is as a point in time short of the first full 1,000,000 cycles. Next the crack dimensions are measured. In one example embodiment, the dimensions of the crack, such as first crack 507, can be measured by an optical microscope on the sides of specimen 501 while the specimen is still attached to the test setup. If crack dimensions exceed the given final crack length $a_c$ and $c_c$, the test is completed and the results are reported. If crack dimensions do not reach $a_c$ and $c_c$, then the test proceeds to the next step. If a crack extension is not detected, the test continues until 1,000,000 cycles are reached and a testing block is considered completed. An example completed testing block that did not experience crack extension is illustrated as testing block 1405 as shown by graph 1401 in FIG. 14. The next step-load is prepared, the cycle count is reset to zero, and the test restarted. The steps are repeated until a crack extension is detected or until "stop-test", whichever comes first, then the constant R testing loop 1101 (FIG. 11) is exited. In the illustrated graph 1401, a crack extension is detected at occurrence 1403, which is as a point in time after two full 1,000,000 cycles, but short completion of the third stepped 1,000,000 cycle testing block.

Figure 15:
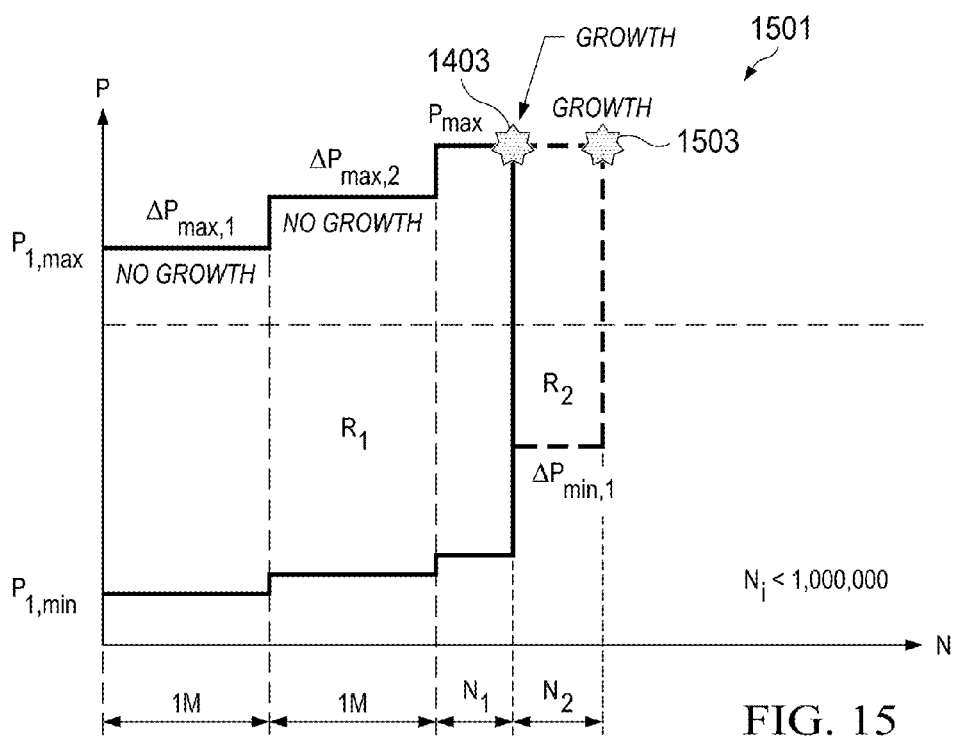
FIG. 15 is a graph, according to one example embodiment.
Figure 16:
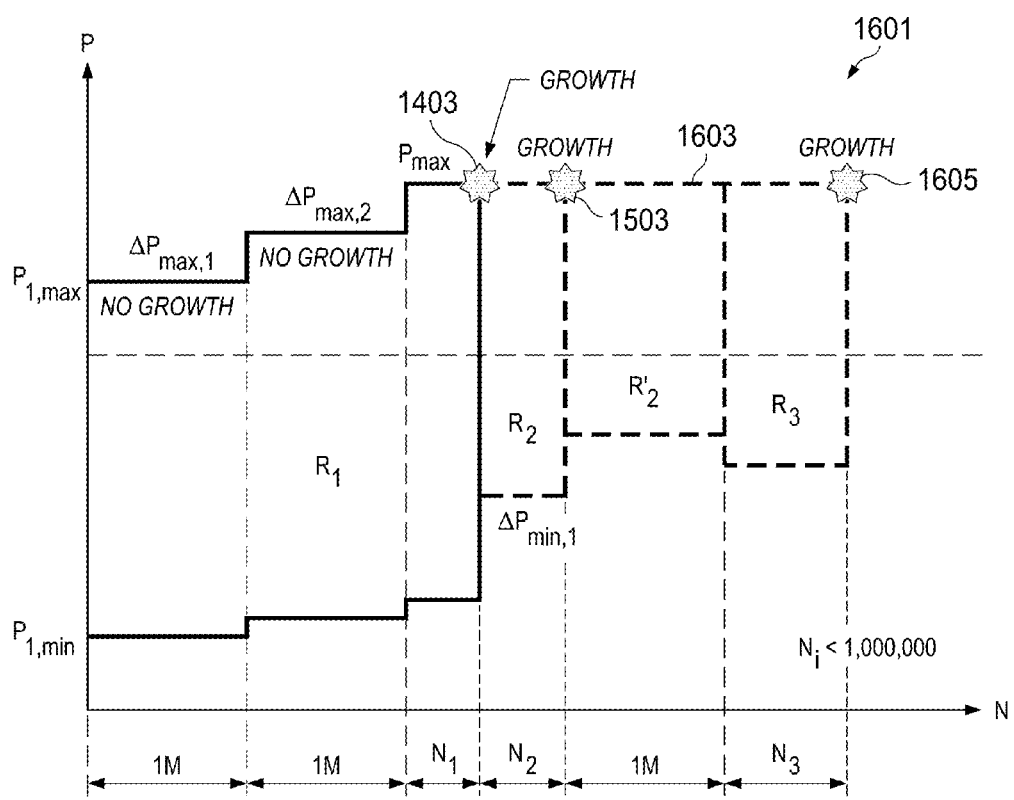
FIG. 16 is a graph, according to one example embodiment.

The constant $P_{max}$ testing loop 1103 with stepped $P_{min}$, constant $P_{max}$, and varying R can include resetting cycle count to zero and resetting loads with an increased $P_{min}$ while keeping the $P_{max}$ the same as that at the constant R loop 1101. Next the test is resumed with cycle count and PD 1201 turned on. If a crack extension is detected at an occurrence 1503 via PD, the test is stopped, as shown in graph 1501 of FIG. 15. Next the extended crack dimension is measured. If the crack dimension exceeds the given final crack length $a_c$ and $c_c$, the test is completed. If the crack dimensions do not reach $a_c$ and $c_c$, then the test continues to the next step. If a crack extension is not detected by PD 1201, the test continues until 1,000,000 cycles are reached at occurrence 1603 and a testing block is considered completed, as shown in graph 1601 of FIG. 16. The results are reported and the process proceeds with the next step-load and instructions. The steps are repeated until a crack extension is detected at an occurrence 1605 or until "stop-test", whichever comes first, then the constant $P_{max}$ testing loop 1103 (FIG. 11) is exited.

Method 201 can also include a step 209 of processing the data from the test. Step 209 is intended to extract the specimen and testing information for each test and determine the validity of the testing result data. Valid data for a threshold testing program can be defined as the data at the crack initiation (or extension) $\Delta a/\Delta N \leq 4 \times 10^{-9}$ in/cycle. If this criterion is met at the crack initiation, the load is valid as a threshold for no-growth. If the threshold criterion is not met at the crack initiation, the previous run-out load can be used instead.

The immediate test data are the no-growth threshold fatigue loads, i.e. maximum load $P_{max}$ and minimum load $P_{min}$, from which fatigue mean and oscillatory load $P_{mean}$ and $P_{osc}$ can be converted:

$$P_{mean} = (P_{max} + P_{min})/2 \quad \text{(Eq. 1)}$$

$$P_{osc} = (P_{max} + P_{min})/2 \quad \text{(Eq. 2)}$$

The no-growth threshold stresses can be calculated as loads divided by notch plane area A:

$$S_{mean} = P_{mean}/A \quad \text{(Eq. 3)}$$

$$S_{osc} = P_{osc}/A \quad \text{(Eq. 4)}$$

Data can be organized in categories of flaw and crack. Under each category, data can be grouped by nominal notch dimensions. In cases where the actual notch/crack length is not the same as nominal length, an adjustment can be made based on geometrical parameter β of Linear Elastic Fracture Mechanics (LEFM):

$$S_{nominal} = S_{actual}(\beta_{actual}/\beta_{nominal})\sqrt{(a_{0,actual}/a_{0,nominal})} \quad \text{(Eq. 5)}$$

For example, in a group of $a_0 = 0.010$-in, the actual notch dimensions can be measured as 0.012, 0.009, 0.010, 0.012, 0.010, 0.008, 0.011, etc. The LEFM adjustment can be made to collapse the non 0.010-in data onto 0.010-in equivalent. Similarly, the data can be adjusted if the crack lengths that are measured during testing are different from the actual crack lengths determined in a post-test measurement.

Table 3 shows an example of organized geometrical and testing results data of a material for a nominal $a_0 = 0.010$-in group. Based on this data table, the threshold loads are determined and the threshold stresses are calculated accordingly.

TABLE 1

Example Data Table of Organized Geometrical and Test Results Data

| Notch Length | Specimen# | 0' - Notch | | 1 | | | | R | N | $P_{max}$ (at break) | $P_{max}$ (previous) | Run-out at last run? | $c_1/c_2$ | $\Delta C$, min | $\Delta C$, max |
|---|---|---|---|---|---|---|---|---|---|---|---|---|---|---|---|
| | | c1 | c2 | c1 | c2 | b1 | b2 | | | | | | | | |
| 0.010 | TR4473-B1-103-1 | 0.0115 | 0.0105 | 0.0160 | 0.0150 | 0.2593 | 0.2607 | −1 | 643,483 | 1,808 | 1,469 | no | 1.095 | 0.0045 | 0.005 |
| | TR4473-B2-103-1 | 0.0100 | 0.0098 | 0.0110 | 0.0110 | 0.2597 | 0.2592 | −1 | 33,370 | 1,900 | 1,543 | no | 1.020 | 0.001 | 0.001 |
| | TR4473-B5-103-3 | 0.0118 | 0.0107 | 0.0210 | 0.0150 | 0.2600 | 0.2600 | 0.05 | 59,278 | 3,087 | 2,487 | no | 1.103 | 0.004 | 0.009 |
| | TR4473-B6-103-3 | 0.0092 | 0.0110 | 0.0130 | 0.0130 | 0.2597 | 0.2606 | 0.05 | 182,745 | 3,205 | 2,787 | no | 0.836 | 0.002 | 0.004 |
| | TR4473-B8-103-3 | 0.0127 | 0.0106 | 0.0127 | 0.0106 | 0.2594 | 0.2603 | 0.05 | 1,000,000 | 2,752 | 2,061 | yes | 1.198 | 0.000 | 0.000 |
| | TR4473-B9-103-4 | 0.0098 | 0.0093 | 0.0098 | 0.0093 | 0.2603 | 0.2604 | 0.50 | 1,000,000 | 4,611 | 3,747 | yes | 1.054 | 0.000 | 0.000 |
| | TR4473-B11-103-5 | 0.0093 | 0.0106 | 0.0093 | 0.0106 | 0.2606 | 0.2606 | 0.74 | 1,000,000 | 6,621 | 0 | yes | 0.877 | 0.000 | 0.000 |
| | TR4473-B11-103-6 | 0.0093 | 0.0106 | 0.0093 | 0.0106 | 0.2606 | 0.2606 | 0.80 | 1,000,000 | 6,621 | 5,857 | yes | 0.877 | 0.000 | 0.000 |

Figure 17:
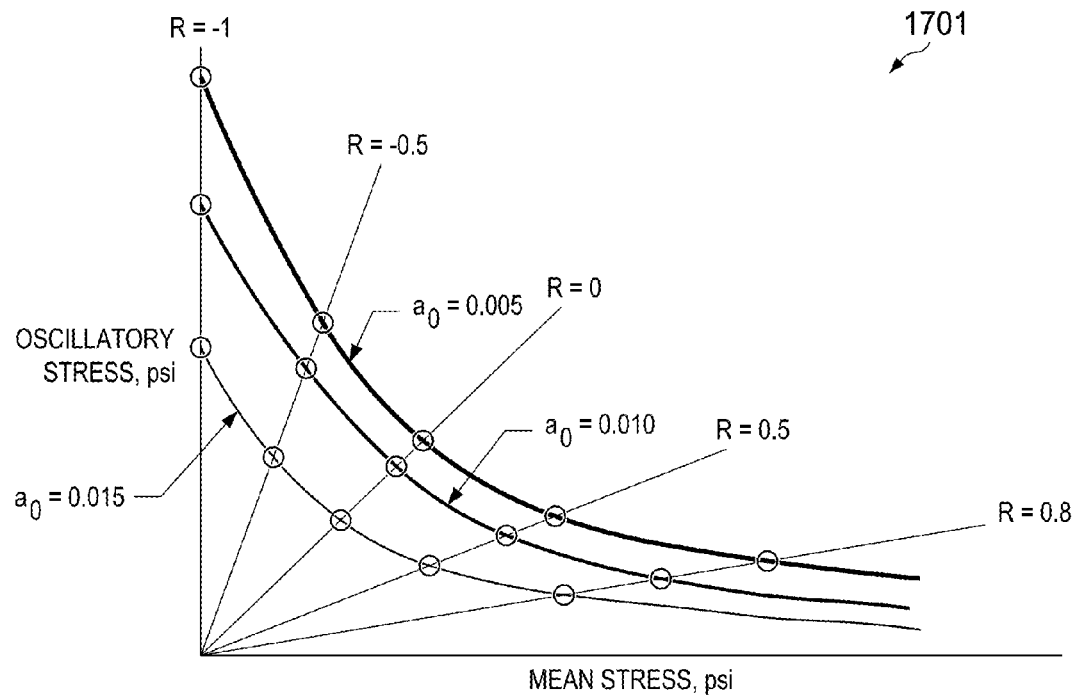
FIG. 17 is a graph, according to one example embodiment.

After data for all groups and categories are analyzed, they can be plotted in a graph 1701 as shown in FIG. 17 as threshold stresses for no-growing flaw and crack for the material. For each flaw/crack length, a curve fit is generated based on the lowest data points.

Referring now to FIG. 4, a method 401 of a designing and manufacturing a part or structure of an aircraft, such as rotorcraft 101, is schematically illustrated. An illustrative structure is bulkhead 113, shown in FIG. 1. A step 403 can include designing a structure with a computer aided design (CAD) tool which can include defining a preliminary geometry of the structure. Step 403 can include performing a stress analysis of the structure, this analysis can include analytically subjecting the structure to loads, calculating the stress, and evaluating the stress with regard to the damage tolerance allowables, the damage tolerance allowables being calculated using method 201 described herein. Step 403 can include iteratively changing the geometry of the part until a weight efficient configuration is reached. In one embodiment, the geometry of the structure is iteratively optimized so as to meet the stress allowables without having unnecessary weight. A step 405 can include manufacturing the structure to the geometry defined in step 403.

Figure 18:
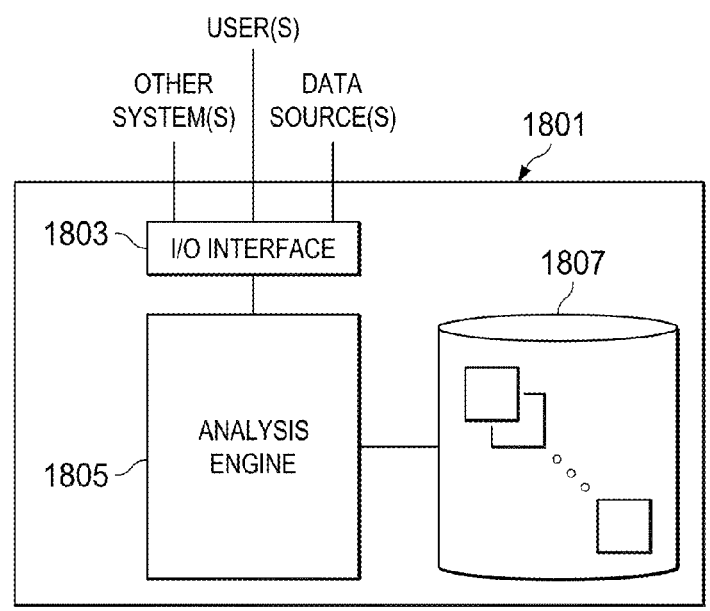
FIG. 18 is a schematic view of a computer system, according to one example embodiment.

Referring now also to FIG. 18, a computer system 1801 is schematically illustrated. Computer system 1801 can be configured for performing one or more functions with regard to the operation of system and method further disclosed herein. Further, any processing and analysis can be partly or fully performed by computer system 1801. Computer system 1801 can be partly or fully integrated with other aircraft computer systems.

The system 1801 can include an input/output (I/O) interface 1803, an analysis engine 1805, and a database 1807. Alternative embodiments can combine or distribute the input/output (I/O) interface 1803, analysis engine 1805, and database 1807, as desired. Embodiments of the system 1801 can include one or more computers that include one or more processors and memories configured for performing tasks described herein. This can include, for example, a computer having a central processing unit (CPU) and non-volatile memory that stores software instructions for instructing the CPU to perform at least some of the tasks described herein. This can also include, for example, two or more computers that are in communication via a computer network, where one or more of the computers include a CPU and non-volatile memory, and one or more of the computer's non-volatile memory stores software instructions for instructing any of the CPU(s) to perform any of the tasks described herein. Thus, while the exemplary embodiment is described in terms of a discrete machine, it should be appreciated that this description is non-limiting, and that the present description applies equally to numerous other arrangements involving one or more machines performing tasks distributed in any way among the one or more machines. It should also be appreciated that such machines need not be dedicated to performing tasks described herein, but instead can be multipurpose machines, for example computer workstations, that are suitable for also performing other tasks.

The I/O interface 1803 can provide a communication link between external users, systems, and data sources and components of the system 1801. The I/O interface 1803 can be configured for allowing one or more users to input information to the system 1801 via any known input device. Examples can include a keyboard, mouse, touch screen, and/or any other desired input device. The I/O interface 1803 can be configured for allowing one or more users to receive information output from the system 1801 via any known output device. Examples can include a display monitor, a printer, cockpit display, and/or any other desired output device. The I/O interface 1803 can be configured for allowing other systems to communicate with the system 1801. For example, the I/O interface 1803 can allow one or more remote computer(s) to access information, input information, and/or remotely instruct the system 1801 to perform one or more of the tasks described herein. The I/O interface 1803 can be configured for allowing communication with one or more remote data sources. For example, the I/O interface 1803 can allow one or more remote data source(s) to access information, input information, and/or remotely instruct the system 1801 to perform one or more of the tasks described herein.

The database 1807 provides persistent data storage for system 1801. While the term "database" is primarily used, a memory or other suitable data storage arrangement may provide the functionality of the database 1807. In alternative embodiments, the database 1807 can be integral to or separate from the system 1801 and can operate on one or more computers. The database 1807 preferably provides non-volatile data storage for any information suitable to support the operation of the system and method disclosed herein, including various types of data discussed further herein. The analysis engine 1805 can include various combinations of one or more processors, memories, and software components.

The particular embodiments disclosed herein are illustrative only, as the system and method may be modified and practiced in different but equivalent manners apparent to those skilled in the art having the benefit of the teachings herein. Modifications, additions, or omissions may be made to the system described herein without departing from the scope of the invention. The components of the system may be integrated or separated. Moreover, the operations of the system may be performed by more, fewer, or other components.

Furthermore, no limitations are intended to the details of construction or design herein shown, other than as described in the claims below. It is therefore evident that the particular embodiments disclosed above may be altered or modified and all such variations are considered within the scope and spirit of the disclosure.

To aid the Patent Office, and any readers of any patent issued on this application in interpreting the claims appended hereto, applicants wish to note that they do not intend any of the appended claims to invoke paragraph 6 of 35 U.S.C. § 112 as it exists on the date of filing hereof unless the words "means for" or "step for" are explicitly used in the particular claim.

The invention claimed is:

1. A method of determining damage tolerance allowables in a specimen, the method comprising:
    preparing the specimen by inducing a notch located in an exterior corner thereof;
    applying an initial cyclic load to the specimen, until a first crack emanating from the notch is detected, the initial cyclic load having an initial maximum load and an initial minimum load;
    applying a subsequent cyclic load to the specimen until extension of the first crack to form a second crack emanating from the first crack is detected, the subsequent cyclic load having a second maximum load and a second minimum load, wherein the second maximum load is the same as the initial maximum load and the second minimum load is greater than the initial minimum load;
    determining a flaw threshold stress based upon the initial maximum load and the initial minimum load for which the first crack starts to emanate from the notch; and
    determining a crack threshold stress for which the second crack grows from the first crack based upon the second maximum load and the second minimum load.

2. The method according to claim 1, wherein the specimen has a square cross-sectional portion and the notch is located in a corner of the square cross-sectional portion.

3. The method according to claim 1, further comprising:
    applying primary cyclic load to a specimen until a number of cycles reaches a predetermined number, the primary cyclic load having a primary maximum load and a primary minimum load.

4. The method according to claim 3, wherein the initial maximum load and the initial minimum load of the cyclic load form an initial load ratio, and wherein the primary maximum load and the primary minimum load of the primary cyclic load form a primary load ratio.

5. The method according to claim 4, wherein the initial maximum load is higher than the primary maximum load.

6. The method according to claim 4, wherein the primary load ratio is equal to the initial load ratio.

7. The method according to claim 1, further comprising: measuring a length of the first crack.

8. The method according to claim 1, further comprising: measuring a length of the second crack.

9. The method according to claim 1, further comprising:
    determining a threshold flaw oscillatory load by adding the initial maximum load and the initial minimum load together and then dividing by two.

10. The method according to claim 9, further comprising:
    determining a threshold stress by dividing the threshold flaw oscillatory load by a plane area of the notch.

11. The method according to claim 10, further comprising:
    designing an aircraft structure based upon the threshold stress.

12. The method according to claim 1, further comprising:
    determining a threshold crack oscillatory load by adding the second maximum load and the second minimum load together and then dividing by two.

13. The method according to claim 12, further comprising:
    determining a threshold stress by dividing the threshold crack oscillatory load by a plane area of the notch.

14. The method according to claim 13, further comprising:
    designing an aircraft structure based upon the threshold stress.

15. The method according to claim 1, further comprising:
    determining a threshold flaw mean load by subtracting the initial minimum load from the initial maximum load and then dividing by two.

16. The method according to claim 15, further comprising:
    determining a threshold stress by dividing the threshold flaw mean load by a plane area of the notch.

17. The method according to claim 1, further comprising:
    determining a threshold crack mean load by adding the second maximum load and the second minimum load together and then dividing by two.

18. The method according to claim 17, further comprising:
    determining a threshold stress by dividing the threshold crack mean load by a plane area of the notch.

* * * * *